(12) United States Patent
Pittaluga et al.

(10) Patent No.: US 11,123,138 B2
(45) Date of Patent: Sep. 21, 2021

(54) MEDICAL DEVICE COMPRISING A HYDROPHILIC CURVED FLEXIBLE TIP FOR THE TREATMENT OF VARICOSE VEINS

(71) Applicants: Paul Pittaluga, Cagnes sur Mer (FR); Sylvain Chastanet, Nice (FR)

(72) Inventors: Paul Pittaluga, Cagnes sur Mer (FR); Sylvain Chastanet, Nice (FR)

( * ) Notice: Subject to any disclaimer, the term of this patent is extended or adjusted under 35 U.S.C. 154(b) by 24 days.

(21) Appl. No.: 15/124,841

(22) PCT Filed: Mar. 11, 2015

(86) PCT No.: PCT/EP2015/000533
§ 371 (c)(1),
(2) Date: Sep. 9, 2016

(87) PCT Pub. No.: WO2015/135647
PCT Pub. Date: Sep. 17, 2015

(65) Prior Publication Data
US 2017/0071670 A1 Mar. 16, 2017

(30) Foreign Application Priority Data

Mar. 12, 2014 (FR) ...................................... 1400596

(51) Int. Cl.
*A61B 18/24* (2006.01)
*A61B 17/12* (2006.01)
(Continued)

(52) U.S. Cl.
CPC ........ *A61B 18/24* (2013.01); *A61B 17/00234* (2013.01); *A61B 17/12186* (2013.01);
(Continued)

(58) Field of Classification Search
None
See application file for complete search history.

(56) References Cited

U.S. PATENT DOCUMENTS 5,782,824 A * 7/1998 Abela .................... A61B 18/24
606/15
6,002,955 A * 12/1999 Willems ............ A61M 25/0041
600/374
(Continued)

FOREIGN PATENT DOCUMENTS

EP    0 921 765 B1    5/2007
EP    2 085 047 A1    8/2009
(Continued)

OTHER PUBLICATIONS

Nehemiah Samuel et al. (2013). Randomized Clinical Trial of Endovenous Laser Ablation Versus Conventional Surgery for Small Saphenous Varicose Veins. Annals of Surgery, 257, 419-426. https://doi.org/10.1097/SLA.0b013e318275f4e4.*

(Continued)

*Primary Examiner* — Allen Porter
*Assistant Examiner* — James Moss
(74) *Attorney, Agent, or Firm* — Seckel IP, PLLC

(57) ABSTRACT

The invention relates to a medical device intended to be inserted into the lumen of a cavity of the human or animal body or in the lumen of a blood vessel. The invention is characterised in that said device comprises a probe (5) suitable for delivering a treatment by the endovenous route, and, at the terminal end thereof, a hooked flexible tip (1), wherein the angle α formed between the extension of the end portion of the probe (5) and the extension of the end portion of the tip (1) is strictly less than +90°, said tip comprising means (3) for delivering a treatment. The invention is particularly applicable to the treatment of varicose veins, reticular veins and spider veins.

12 Claims, 2 Drawing Sheets

(51) Int. Cl.
*A61B 18/14* (2006.01)
*A61M 25/00* (2006.01)
*A61B 17/00* (2006.01)
*A61B 18/18* (2006.01)
*A61B 18/00* (2006.01)
*A61B 18/04* (2006.01)

(52) U.S. Cl.
CPC ...... *A61B 18/1492* (2013.01); *A61B 18/1815* (2013.01); *A61M 25/00* (2013.01); *A61M 25/007* (2013.01); *A61M 25/0069* (2013.01); *A61M 25/0074* (2013.01); *A61B 2017/003* (2013.01); *A61B 2017/00778* (2013.01); *A61B 2017/00942* (2013.01); *A61B 2017/1205* (2013.01); *A61B 2018/00279* (2013.01); *A61B 2018/00404* (2013.01); *A61B 2018/00577* (2013.01); *A61B 2018/044* (2013.01); *A61B 2018/1422* (2013.01); *A61B 2018/1861* (2013.01)

(56) References Cited

U.S. PATENT DOCUMENTS

| | | | | |
|---|---|---|---|---|
| 6,251,104 | B1 | 6/2001 | Kesten et al. | |
| 6,280,434 | B1* | 8/2001 | Kinoshita | A61M 25/0041 600/435 |
| 6,493,590 | B1* | 12/2002 | Wessman | A61N 1/0534 607/116 |
| 6,592,575 | B1 | 7/2003 | Kesten et al. | |
| 6,689,127 | B1 | 2/2004 | Gough et al. | |
| 2004/0015151 | A1* | 1/2004 | Chambers | A61M 25/0041 604/532 |
| 2007/0066878 | A1* | 3/2007 | Worley | A61M 25/008 600/374 |
| 2007/0179496 | A1 | 8/2007 | Swoyer et al. | |
| 2009/0082760 | A1* | 3/2009 | Zinn | A61B 18/22 606/15 |
| 2010/0125284 | A1 | 5/2010 | Tanner et al. | |
| 2012/0136350 | A1 | 5/2012 | Goshgarian et al. | |
| 2013/0172786 | A1* | 7/2013 | Olson | A61M 25/0041 600/587 |
| 2014/0128844 | A1* | 5/2014 | Kornowski | A61M 25/0009 604/509 |
| 2015/0051467 | A1* | 2/2015 | Corbucci | A61B 5/7282 600/381 |

FOREIGN PATENT DOCUMENTS

| | | |
|---|---|---|
| EP | 2 477 571 B2 | 5/2016 |
| WO | 99/22797 A1 | 5/1999 |
| WO | 03/041603 A1 | 5/2003 |
| WO | 2012/160562 A1 | 11/2012 |

OTHER PUBLICATIONS

Circulation Foundation, "Varicose Veins—Endovenous Laser Therapy", https://web.archive.org/web/20120627135556/https://www.circulationfoundation.org.uk/help-advice/veins/varicose-veins-endovenous-laser-therapy, dated Jun. 27, 2012, viewed on Nov. 21, 2020.*

International Search Report and Written Opinion dated Aug. 21, 2015 issued in corresponding application No. PCT/EP2015/000533; in English (10 pages).

French Search Report and Written Opinion dated Nov. 11, 2014 issued in priority French application No. FR1400596 (with English machine translation; 14 pages) D4, US20100125284 cited in the French Search Report is not listed in this IDS since it was already listed in the IDS filed Sep. 9, 2016.

* cited by examiner

MEDICAL DEVICE COMPRISING A HYDROPHILIC CURVED FLEXIBLE TIP FOR THE TREATMENT OF VARICOSE VEINS

The present invention relates to a hooked flexible tip and a medical device comprising, at the end portion thereof, such a hooked flexible tip. This tip and this device comprising this tip are suitable for being inserted into the lumen of a cavity of the human body or into the lumen of a blood vessel. More particularly, the invention relates to a tip or a medical device intended to be inserted into the lumen of a blood vessel, for treating varicose disease and particularly varicose veins.

Dysplastic veins or varicose veins are generally sinuous dilations of superficial veins, which are more than 3 mm in diameter when the patient is in the upright position.

They are due to valve dysfunction giving rise to a backflow of blood: the blood no longer flows upwards to the heart, but downwards to the feet. Varicose veins are referred to as saphenous varicose veins when they relate to the saphenous trunks or the direct collaterals thereof. The great and small saphenous veins also have tributary veins which may also be varicose. A vein is described as tributary in respect of another vein when it is on one of the branches thereof, i.e. one of the inflowing veins thereof.

Various techniques are now available for treating varicose veins. The main treatment of varicose veins consists of ablation by extracting the diseased veins and particularly the saphenous trunks. Since the 2000s, less aggressive, endovenous treatments have been used to treat large diseased trunks. Progress in knowledge over the last ten years has helped highlight the importance of treating varicose tributaries, i.e. branches of the main trunks, and not merely removing the saphenous vein for the treatment of varicose disease. Various studies have demonstrated that varicose veins could exist without the presence of a backflow in the saphenous vein and also, removing the saphenous vein did not necessarily prevent the recurrence of varicose veins on previously healthy tributaries. Furthermore, studies have demonstrated that the ablation of varicose veins on tributaries of the saphenous vein concomitantly with removal of the saphenous vein gave longer-lasting results.

Finally, further studies have demonstrated that excision, thus ablation of varicose tributaries without ablation of the saphenous vein, helped eliminate backflow.

From the end of the 1990s, some companies have developed endovenous probes for obliterating a vein, totally or partially, with a permanent and long-term effect. For this, these probes deliver different types of thermal energies particularly obtained from laser, radiofrequency, steam or microwaves. Immediate proximity or direct contact of a heat source with the vein wall appears to be essential for obtaining permanent and long-term vein obliteration. It is thus important to be able to advance the probe as close to the area to be obliterated as possible. Various probes of different lengths, rigidities and diameters are available on the market. Furthermore, studies have demonstrated the efficacy of these devices for permanent and long-term obliteration of the treated veins.

The document EP0921765 discloses such a system using a catheter applying energy to reduce the diameter of a vein. The varicose vein treatment procedure using this system is commonly known as the Closure™ procedure. This procedure is performed on an outpatient basis under local or general anaesthetic and comprises three main steps:

(i) a first step for mapping the saphenous vein enabling the practitioner to determine the site where the catheter is to be inserted and mark the desired position of the end of the catheter for commencing treatment;

(ii) a second step for inserting the catheter into the saphenous vein;

(iii) a third step for emitting RF radiofrequencies for heating the vein wall to a target temperature of approximately 120° C., and then removing the catheter.

However, this procedure is only suitable for treating relatively straight veins. It is thus only suitable for obliterating the great saphenous vein or the small saphenous vein, but is not suitable for treating tributary veins which are generally sinuous and smaller in diameter than saphenous veins.

A further solution has been developed, consisting of diffusing steam in a vein segment from a puncture point. In this way, the document EP2477571 describes a venous therapy device using steam generated by a hot-tip laser.

This technique makes use of a short catheter for catheterising varicose tributaries to inject steam therein in order to obliterate them. However, in practice, this diffusion proves to be very limited in terms of distance and gives results which are not satisfactory. Even though it is theoretically possible to diffuse steam in a vein segment from a puncture point, this diffusion is relatively limited in terms of distance. Furthermore, the straight shape of the catheter makes it unsuitable for advancing through sinuous sections.

In addition, for the treatment of varicose tributary veins, current treatments require more precise technologies such as surgical excision or direct-injection obliteration.

Surgical excision, i.e. ambulatory phlebectomy, is a technique not requiring hospitalisation. This technique consists of removing superficial varicose veins under local anaesthetic. Ambulatory phlebectomy is reserved for some types of varicose veins, after precise location by means of the Doppler echo technique. The varicose veins are removed with clips or hooks, via tiny incisions of 1 to 2 millimetres.

Direct-injection obliteration, i.e. sclerotherapy, is a technique consisting of injecting into the varicose veins, using a needle, a substance irritating the inner vessel wall. The sclerosing agent may be injected in liquid form or in emulsion ("sclerosing foam").

However, the current techniques for treating varicose tributary veins, phlebectomy or sclerotherapy, involve some drawbacks. Phlebectomy, although a very precise, effective and long-lasting technique, requires numerous skin incisions to extirpate the varicose veins and varicose tributary veins. Furthermore, this technique is difficult, long and tedious to perform. Sclerotherapy or sclerosis for its part is performed with no incisions but is less effective, less long-lasting, less selective and may induce inflammation of the vein and subcutaneous tissue. Furthermore, this technique is not applicable to all vein sizes.

Therefore, there is presently a need to develop means for treating all types of varicose veins, including sinuous varicose tributaries, simply, quickly and in a manner minimising incisions.

It is currently technically very difficult or impossible to catheterise varicose tributaries and advance current endovenous devices (optical fiber, radiofrequency probe or steam catheter) therein, essentially due to the sinuous sections and irregular diameters of tributary veins. As mentioned above, only saphenous veins or straight tributaries can be treated by the endovenous thermal process.

The solution for the stated problem relates to a medical device intended to be inserted into the lumen of a cavity of the human or animal body or into the lumen of a blood vessel, wherein it comprises, at the terminal end thereof, a hooked flexible tip comprising means for delivering a treatment.

Surprisingly, the applicants succeeded in demonstrating that it was possible to advance and bring such a medical device into contact both with varicose veins and sinuous varicose tributary veins, situated on the tributaries (collaterals) of saphenous veins. Fitting a pre-existing medical device for venous therapy with a part which is a hooked flexible tip makes it possible to advance said device in an anterograde and retrograde fashion in the lumen of a blood vessel.

The hooked flexible tip has properties enabling it to overcome sinuous segments, variations in diameter and bifurcations in order to deliver energy, particularly thermal energy, in direct contact with or in the immediate vicinity of the vein wall. This enables for example permanent and long-term obliteration of the vein segment treated.

The invention secondly relates to a hooked flexible tip associated or integrated with a medical device according to the invention.

The invention thirdly relates to a method for treating varicose veins, reticular veins and/or spider veins, by applying energy by means of a medical device suitable for insertion in the lumen of a cavity of the human or animal body or in the lumen of a blood vessel, wherein said medical device comprises, at the terminal end thereof, a hooked flexible tip comprising means for delivering a treatment.

The invention will be understood more clearly on reading the following non-limiting description, with reference to the appended figures, wherein.

Figure 1A:
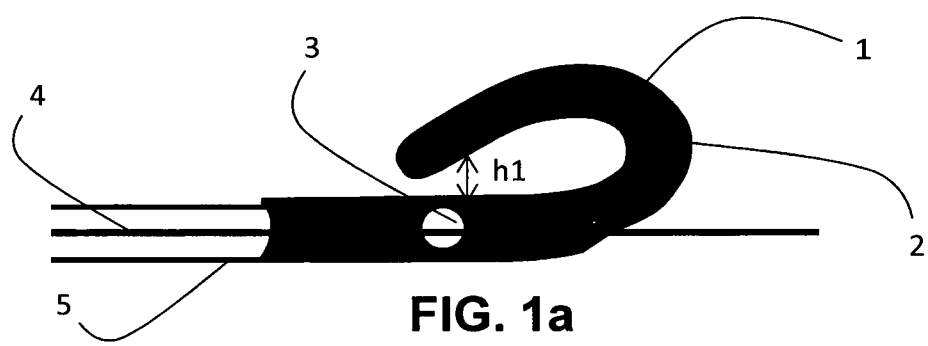
FIGS. 1a to 1c represent profile views of the end portion of the medical device according to the invention comprising a hooked flexible tip.

The present invention proposes the addition to a medical device of a hooked flexible tip having technical features enabling it to advance in an anterograde and retrograde manner in the lumen of a cavity of the human or animal body or in the lumen of a blood vessel. In other words, the hooked flexible tip is a mounted part added to a medical device according to the invention.

Alternatively, the invention suggests integrating in a medical device, a hooked flexible tip having technical features enabling it to advance in an anterograde and retrograde manner in the lumen of a cavity of the human or animal body or in the lumen of a blood vessel. In this way, the hooked flexible tip may also be a part directly integrated in a medical device according to the invention.

The human body has a dorsal cavity and a ventral cavity. In the dorsal cavity:
the cranial cavity contains the brain, the eyes and the ears and associated biological conduits; and
the spinal cavity comprises the spinal cord and associated biological conduits.
In the ventral cavity:
the rib cage contains the lungs, heart and associated biological conduits;
the abdominal cavity contains the kidneys, urethra, stomach, intestines, liver, pancreas, gallbladder and associated biological conduits;
the pelvic cavity contains the bladder, anus, reproductive system and associated biological conduits.

The medical device is suitable for being inserted into the lumen of one of the cavities of the human body described above or in one of the equivalent cavities of the body of an animal.

Advantageously, the medical device according to the invention is suitable for advancing in the lumen of biological conduits wherein it is not easy or possible to access, due to physical and/or topographic constraints. For example, the device according to the invention can advance in the bile duct or in the urinary tract.

Furthermore, the medical device according to the invention is particularly suitable for advancing in the lumen of a blood vessel, i.e. in biological conduits such as veins and arteries, transporting blood in the body of a human or animal.

The medical device is suitable for treating various biological conduits, in particular:
(1) obliterating treated vein segments in order to exclude them from the venous circulation;
(2) repairing biological conduits such as a vein wall; or
(3) delivering therapeutic substances into biological conduits.

More preferentially, the medical device according to the invention is intended to be inserted into the lumen of a blood vessel, to apply energy in order to reduce the diameter of a vein for treating varicose veins, reticular veins and spider veins. Even more preferentially, the medical device is suitable for treating varicose veins.

As illustrated in FIGS. 1a, 1b, 1c and 2, to be able to deliver the sought treatment in the lumen of a cavity of the human or animal body, or in the lumen of a blood vessel, the medical device according to the invention comprises a probe 5 which is suitable for delivering a treatment by the endovenous route.

Preferably, said probe 5 is chosen from laser probes, catheters, radiofrequency probes, steam probes or microwave probes.

More preferably, the medical device according to the invention comprises a laser probe, a catheter or a radiofrequency probe.

Even more preferentially, the medical device according to the invention comprises, by way of a laser probe 5 for diffusing a laser beam 4, a laser optical fiber such as for example the ELVeS™ brand fiber manufactured by BIOLITECT™.

The invention secondly relates to a hooked flexible tip associated or integrated with a medical device according to the invention.

Figure 1B:
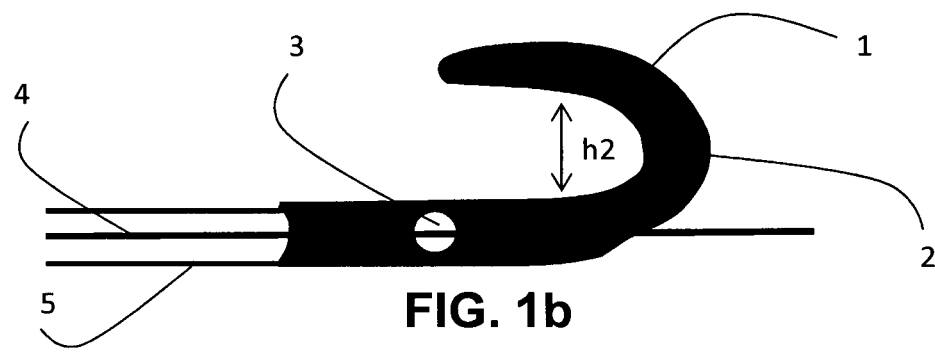
Figure 1C:
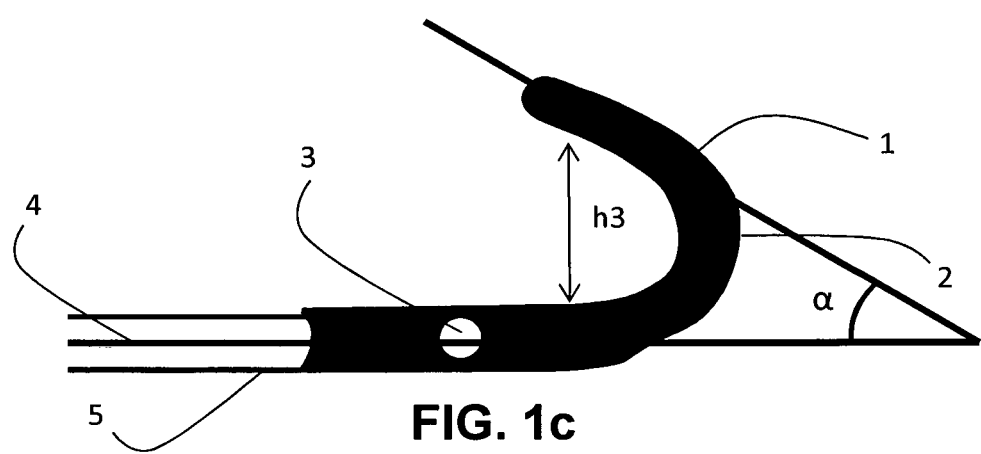

As illustrated in FIGS. 1a, 1b and 1c, the flexible tip 1 is hooked, i.e. by default, thus when it is not subject to any load, it is curved in the shape of a hook. In this way, as illustrated in FIG. 1c, the angle α formed between the extension of the end portion of the probe 5 and the extension of the end portion of the tip 1 is strictly less than +90°. Preferably, this angle α is between +45° and −45°. More preferably, this angle is between +30° and −30°.

The tip is flexible, i.e. it is capable of adapting to the biological conduits wherein it advances by bending or yielding. FIGS. 1a to 1c illustrate the type of curvature that may be adopted by the hooked flexible tip. In this way, the height h1 h2 and h3 between the terminal end of the tip and the probe may vary according to the biological conduit wherein the medical device is to move.

Figure 2:
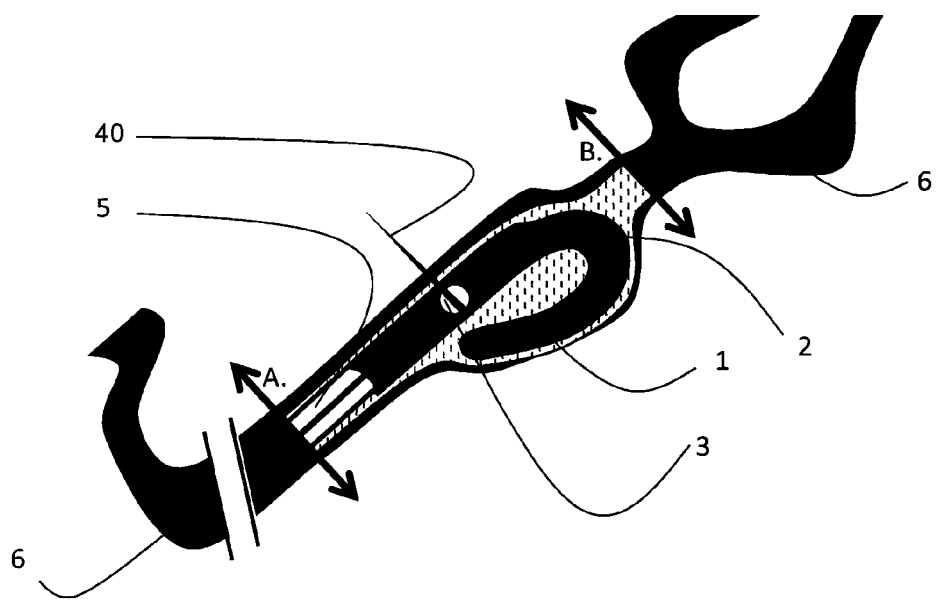
FIG. 2 represents a varicose vein or tributary in the lumen whereof, along the section AB, the end portion of the medical device according to the invention comprising a hooked flexible tip can be seen to advance.
Figure 3:
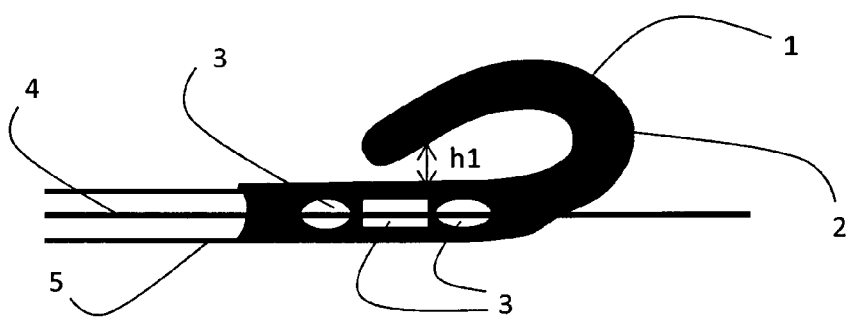
FIG. 3 represents a profile view of the end portion of the medical device according to the invention comprising a hooked flexible tip with a plurality of orifices.

The advantage of the curvature of the tip 1 is that it enables the device to have an atraumatic curve terminal end 2. Such a curved end 2 prevents the perforation or injury of the biological conduit 6 wherein the medical device is capable of advancing, as illustrated in FIG. 2.

Of the materials suitable for use for manufacturing the tip, those skilled in the art may use any flexible, pliable and/or deformable material, suitable for advancing a medical device in a biological conduit, preferentially in the lumen of blood vessels.

By way of a non-limiting example of materials suitable for use, mention may be made of thermoplastic polymers, elastomers, thermoplastic elastomers, silicones, latex and rubber.

Preferably, the materials suitable for use are polymers or elastomers having a Shore hardness between 25 and 70 Shore A.

Even more preferentially, the materials are particularly chosen from biocompatible materials having the property of being well-tolerated by the body, such as silicones, polyurethanes or polytetrafluoroethylene PTFE.

The size and diameter of the flexible tip are dependent on the biological conduits wherein they are required to move.

Preferably, the total length of the flexible tip, i.e. the length of the extended tip, is between 1 mm and 100 mm. More preferably, the total length of the flexible tip is between 5 mm and 50 mm. Even more preferentially, the total length of the flexible tip is between 10 mm and 30 mm.

Preferably, the mean outer diameter of the flexible tip is between 0.3 Fr (for French Gauge) and 60 Fr, i.e. between 0.10 mm and 20 mm. More preferably, the mean outer diameter of the flexible tip is between 2 Fr and 20 Fr, i.e. between 0.67 mm and 6.7 mm. Even more preferentially, the outer diameter of the flexible tip is between 3 Fr and 9 Fr, i.e. between 1 mm and 3 mm.

According to the invention, the tip comprises one or a plurality of means for delivering a treatment, particularly on the areas to be treated. The treatment according to the invention may consist of administering active and/or therapeutic substances, or of diffusing a heat source.

The treatment may for example consist of repairing the vein wall, unclogging a vein segment, embolising a lesion or even delivering an active and/or therapeutic substance in situ.

Preferably, the administration of active and/or therapeutic substances, or diffusion of a heat source is suitable for treating varicose veins, reticular veins and spider veins. In this way, the medical device according to the invention is suitable for example for obliterating vein segments in order to exclude them from the venous circulation.

As illustrated in figures 1a, 1b, 1c, 2 and 3, the hooked flexible tip 1 comprises means for delivering a treatment which is preferentially an opening represented by at least one lateral orifice 3. Said lateral orifice(s) 3 may be of different shapes and sizes.

Preferably, said lateral orifice(s) 3 are particularly in the shape of a circle, triangle, square, rectangle, trapezium, diamond, oval. Preferably, the lateral orifice(s) 3 are substantially circular and the mean diameter thereof is between 0.33 Fr (for French Gauge) and 20 Fr, i.e. between 0.1 mm and 6.7 mm. More preferably, the mean diameter of the lateral diameter(s) 3 is between 1 Fr and 10 Fr, i.e. between 0.33 mm and 3.3 mm.

When the means for delivering a treatment is an opening represented by a plurality of lateral orifices 3, the number thereof is preferentially between 2 and 20. More preferably, the number of lateral orifices 3 is between 2 and 10. Even more preferentially, the lateral orifices 3 are 2, 3, 4, 5, 6, 7 or 8 in number.

According to the invention, to facilitate the progression of the medical device according to the invention in the biological conduits, the flexible tip is preferentially made of a hydrophilic material or coated with a hydrophilic layer.

The applicants succeeded in demonstrating the curved shape of the tip 1, the pliability thereof and the hydrophilic properties thereof enable anterograde and retrograde progression of the medical device according to the invention particularly via sinuous, irregular varicose veins of irregular diameter; along with the passage of bifurcations, so as to deliver the treatment along the entire segment of the biological conduit, for example a vein.

In order to be able to dispense thermal energy, the device according to the invention comprises a heating module suitable for heating a target area of the biological conduits. This heating module is suitable for diffusing for example a laser, generating a radiofrequency, diffusing steam or supplying microwave energy. In this way, this heating module may contribute to the delivery of the sought treatment, for example the permanent and long-term obliteration of the venous lumen, suitable for excluding the treated vein segment from the circulation.

According to one preferred embodiment of the invention, the heating module is suitable for diffusing a laser beam 4.

According to one particular embodiment of the invention, the medical device is intended to be inserted into the lumen of a blood vessel, to apply energy so as to reduce the diameter of a vein for the treatment of varicose veins, said device comprising at the terminal end thereof, a hooked flexible tip 1 comprising a lateral orifice 3 for diffusing a heat source which is a laser beam 40 as illustrated on FIG. 2. This laser diffusion is suitable for closing the vein. Endovenous laser vein closure is based on a thermal action of the laser. This thermal action is a complex process consisting of three steps: converting light into heat; transferring heat from the primary volume: the blood, to the secondary volume: the vein wall; and thermochemical denaturing of the tissue constituents of the vein wall.

The invention also relates to a method for treating varicose veins, reticular veins and/or spider veins, by applying energy by means of a medical device suitable for insertion in the lumen of a cavity of the human or animal body or in the lumen of a blood vessel, wherein said medical device comprises, at the terminal end thereof, a hooked flexible tip comprising means for delivering a treatment.

More preferably, the invention relates to a method for treating varicose veins, reticular veins and/or spider veins, by applying energy by means of a medical device suitable for insertion in the lumen of a cavity of the human or animal body or in the lumen of a blood vessel, wherein said medical device comprises a probe 5 suitable for delivering a treatment by the endovenous route, and, at the terminal end thereof, a hooked flexible tip 1, wherein the angle α formed between the extension of the end portion of the probe 5 and the extension of the end portion of the tip 1 is strictly less than +90°, said tip comprising means for delivering a treatment.

The present invention will now be illustrated by means of the following examples:

EXAMPLE 1

Example of Flexible Forked Tip According to the Invention

The flexible forked tip has the following features:
Name of prototype: Slalom
total length of flexible tip: 30 mm
outer diameter of flexible tip: 6 Fr (2 mm)
diameter of lateral orifice: 3 Fr (1 mm)
tip components: polytetrafluoroethylene.

EXAMPLE 2

Example of Flexible Forked Tip According to the Invention

The flexible forked tip has the following features:
Name of prototype: Slalom
total length of flexible tip: 20 mm
outer diameter of flexible tip: 3 Fr (1 mm)
diameter of lateral orifice: 1.5 Fr (0.5 mm)
tip components: silicone.

EXAMPLE 3

Example of Medical Device According to the Invention

The medical device comprises firstly:
a probe
and secondly:
a tip as described in example 1.

This medical device is connected to a heating device for heating a treatment area in order to reduce the diameter of a blood vessel and/or obliterate a blood vessel.

The medical device thus consists of an optical fiber and a flexible hooked tip, and is suitable for carrying a laser beam of a suitable wave frequency for the target which is in this case a vein wall, so as to deliver the sought treatment, for example the permanent and long-term obliteration of the vein lumen so as to exclude the treated vein segment from the circulation.

To introduce the device into a vein, the vein is catheterised percutaneously with a needle or a short catheter, or via a very short direct approach. Inserting the device detailed above inside the vein may be performed directly or using a small insertion device.

Then, the device is advanced as close to the vein segment to be treated as possible.

The progression of the device may be monitored in a direct visual manner through the skin via a light emitted at the end thereof (transillumination) and/or by perioperative ultrasonographic monitoring.

The treatment is delivered sequentially or continuously within the vein segment by progressively removing the device.

Finally, the complete treatment of the target vein segment(s) is performed via one or a plurality of insertion points determined according to the preoperative clinical and ultrasonographic location and according to the progression distance of the device.

EXAMPLE 4

Example of Flexible Forked Tip According to the Invention

The flexible forked tip has the following features:
Name of prototype: Slalom
total length of flexible tip: 30 mm
outer diameter of flexible tip: 6 Fr (2 mm)
number of lateral orifices: 4
diameter of lateral orifices: 1 Fr (0.33 mm)
tip components: polytetrafluoroethylene.

The invention claimed is:

1. Medical device intended to be inserted into a lumen of varicose veins having at least one of sinuosity or irregular diameter of a human or animal body, for treatment of said varicose veins, wherein the device consists essentially of:
a probe suitable for delivering a treatment of the varicose veins by an endovenous route, and,
at a terminal end of the probe, a hooked flexible tip consisting essentially of a hooked flexible tip portion and means for delivering a treatment,
wherein the hooked flexible tip has a shape of a hook in absence of any load and includes a proximal portion, an end portion, and a curved portion between the proximal portion and the end portion, wherein an angle α between an extension of an end portion of the probe and an extension of the end portion of the tip is less than +90° in absence of any load,
wherein the means for delivering a treatment is in the proximal portion of the hooked flexible tip and wherein the end portion of the hooked flexible tip is located outside of a diameter of the proximal portion at the means for delivering a treatment,
wherein the hooked flexible tip is configured so that a distance between a terminal end of the end portion and the probe is capable of varying according to at least one of sinuosity or variation of diameter of varicose veins when progressing under an anterograde or retrograde manner in a lumen of the varicose veins, and
wherein the hooked flexible tip is made of flexible, pliable and/or deformable material selected from the group consisting of thermoplastic polymers, elastomers, thermoplastic elastomers, silicones, latex and rubber.

2. The medical device according to claim 1, wherein the angle α is between +45° and −45°.

3. The medical device according to claim 2, wherein the probe is chosen from laser probes, catheters, radiofrequency probes, steam probes or microwave probes.

4. The medical device according to claim 1, intended to be inserted into the lumen of a blood vessel, to apply energy so as to reduce a diameter of a vein for a treatment of varicose veins, reticular veins and spider veins, wherein a total length of the tip is in a range of from 1 mm to 100 mm, and an outer diameter of the tip is in a range of from 0.10 mm to 20 mm.

5. The medical device according to claim 1, wherein the means for delivering a treatment comprises a lateral orifice for diffusing a heat source to perform endovenous thermal obliteration.

6. The medical device according to claim 1, wherein the means for delivering a treatment is a lateral orifice for diffusing a heat source to perform endovenous thermal obliteration.

7. The medical device according to claim 1, wherein the means for delivering a treatment consists of 2 to 20 lateral orifices for diffusing a heat source to perform endovenous thermal obliteration.

8. The medical device according to claim 1, wherein the tip consists of materials chosen from polymers or elastomers having a Shore hardness in a range of from 25 to 70 Shore A.

9. The medical device according to claim 1, wherein a total length of the tip is in a range of from 1 mm to 100 mm, and an outer diameter of the tip is in a range of from 0.10 mm to 20 mm.

10. The medical device according to claim 9, intended to be inserted into the lumen of a blood vessel, for treatment of varicose veins, wherein the length of the tip is in a range of from 5 mm to 50 mm, and a diameter of the tip is in a range of from 0.67 mm to 6.7 mm.

11. The medical device according to claim 1, comprising a heating module capable of dispensing a thermal energy treatment.

12. The medical device according to claim 11, wherein the heating module is a laser module and the thermal energy treatment is a laser beam treatment.

\* \* \* \* \*